US00PP30955P2

(12) United States Plant Patent
Olesen et al.

(10) Patent No.: US PP30,955 P2
(45) Date of Patent: Oct. 22, 2019

(54) ***CLEMATIS* PLANT NAMED 'EVIPO092'**

(50) Latin Name: *Clematis viticella*
Varietal Denomination: Evipo092

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/999,899

(22) Filed: Sep. 10, 2018

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

(56) References Cited

PUBLICATIONS

PLUTO Plant Database Variety Apr. 11, 2019.*

* cited by examiner

*Primary Examiner* — Annette H Para

(57) ABSTRACT

A new *Clematis* plant with a compact growth habit, profuse, red purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo092'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2006 and the resulting seeds were planted the following winter in a controlled environment in Guernsey, Channel Islands, United Kingdom. The new variety named 'Evipo092' originated as a single seedling from the stated cross.

The new *clematis* plant may be distinguished from its female seed parent and male pollen parent by the following characteristics. The female seed parent has flowers over 100 mm in diameter, while the new variety has flowers with a diameter between 80 and 100 mm. The male seed parent has Red Purple 60C colored tepals while the new variety has Red Purple 59B colored tepals.

The objective of the hybridization of this *clematis* plant was to create a new and distinct variety for nursery culture with unique qualities such as:

1. Uniform and abundant red purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo092' was selected by Mogens N. Olesen and Raymond J. Evison in their *clematis* development program in the Channel Islands, United Kingdom in 2007. Asexual reproduction of 'Evipo092' by means of vegetative cuttings and traditional layering was first performed by Mogens N. Olesen and Raymond J. Evison in the nursery during the summer of 2007. This initial and subsequent asexual propagations have demonstrated that the characteristics of 'Evipo092' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo092'.

Specifically illustrated in FIG. 1 of the drawings are open flowers, flower buds at various stages of development, tepals detached showing reproductive flower parts, and a seed head.

DETAILED DESCRIPTION OF THE VARIETY

Figure 1:
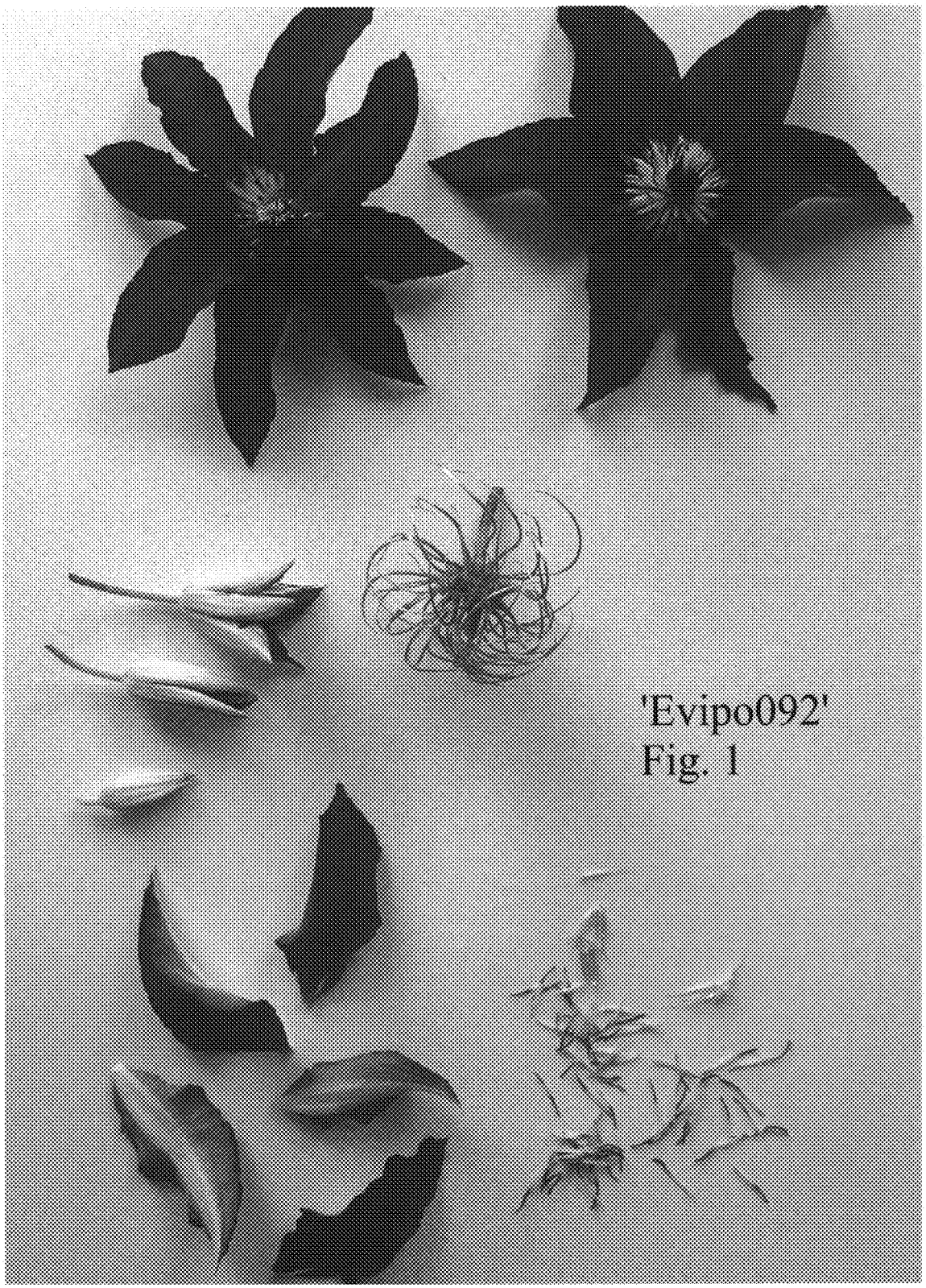
Figure 2:
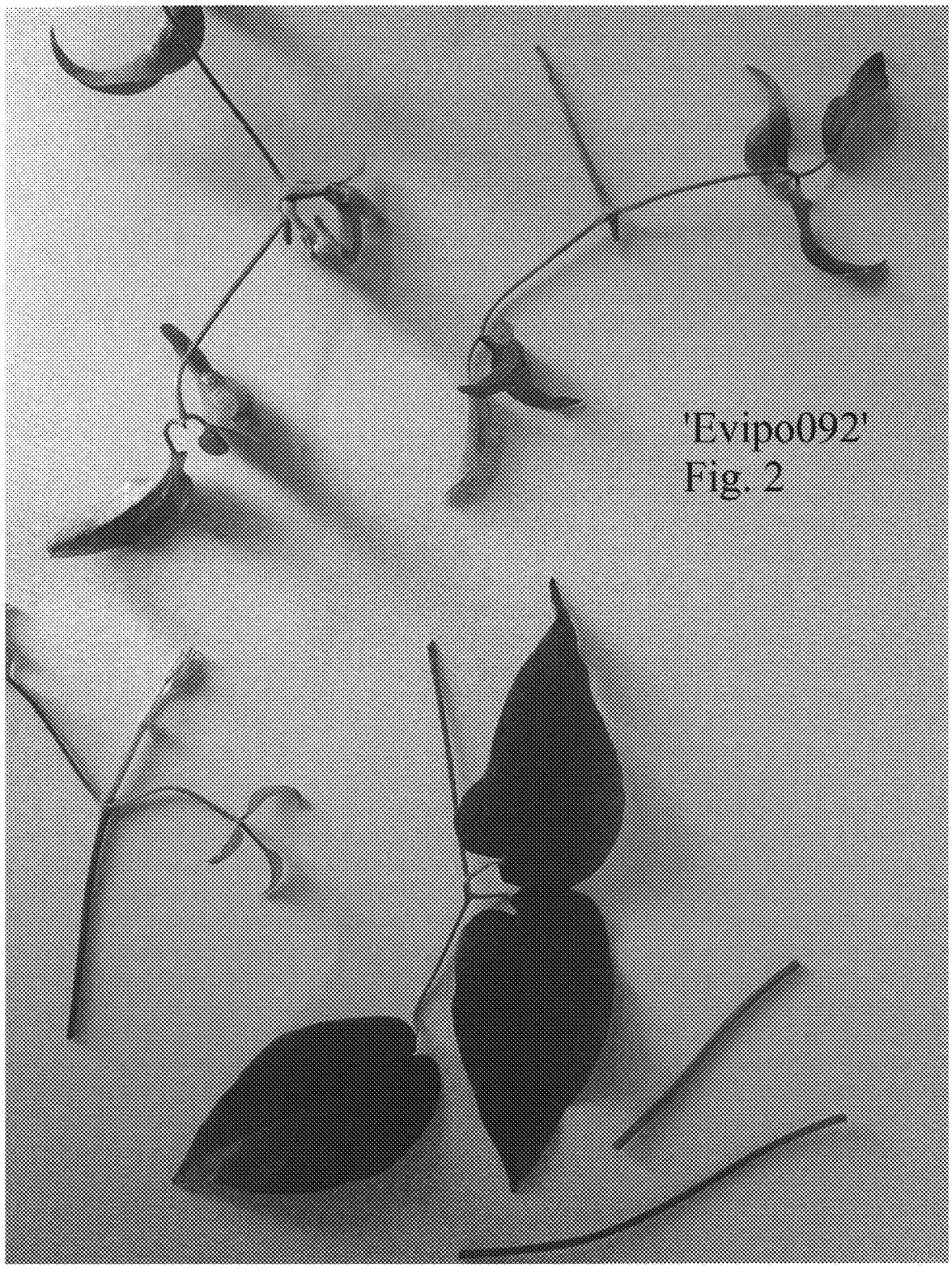
FIG. 2 shows mature and juvenile leaves and stems. Illustrated plants are 2 years of age.

The following is a detailed description of 'Evipo092', as observed in its growth throughout the flowering period in Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo069' described and illustrated in U.S. Plant Pat. No. 27,714 are compared to 'Evipo092' in Chart 1.

CHART 1

| | 'Evipo092' | 'Evipo069' |
|---|---|---|
| Tepal overlap | almost none | slightly |
| Tepal upper surface after opening | Red-Purple Group 59B | Red-Purple Group 59A |
| Tepal shape | lanceolate | ovate |

FLOWER AND FLOWER BUD

Blooming habit: Recurrent. The natural flowering period is generally from April to September.

Flower bud:
- *Size.*—Normally 22 mm in length. Bud diameter is 8 mm.
- *Bud form.*—Long and elliptic.
- *Bud color.*—Yellow-Green Group 145C with intonations of Greyed-Purple Group 186C toward the apex.
- *Texture.*—Pubescent.

Pedicel:
- *Surface texture.*—Smooth, pubescent.
- *Length.*—15 to 40 mm in length with 2 mm diameter.
- *Color.*—Yellow-Green Group 145A.
- *Strength.*—Moderately strong.

Receptacle:
- *Surface texture.*—Lightly pubescent.
- *Shape.*—Broad funnel.
- *Size.*—1 mm (h)×3 mm (w).
- *Color.*—Yellow-Green Group 145A.

Flower arrangement:
- *Location on vine.*—New growth only.
- *Borne.*—Single flower bud development at the leaf axillary.

Flower bloom:
- *Size.*—On average, flowers are 80 to 100 mm in diameter and 15 mm in depth.
- *Profile.*—Open flowers are flattened convex.
- *Fragrance.*—None.
- *Lasting quality.*—Flowers normally remain up to 10 days on the plant.

Tepals:
- *Tepal color.*—Upon opening, the upper surface is Red-Purple Group 59B. The lower surface is Greyed-Purple Group 186A with a stripe the color of Yellow-Green Group 144D. After opening, the upper surface is Red-Purple Group 59B. The lower surface is Greyed-Purple Group 186A with a stripe of Yellow-Green Group 145D.
- *Quantity.*—Normally 6 tepals.
- *Size.*—40 to 55 mm in length by 20 to 30 mm wide.
- *Shape.*—Individual tepal shape is lanceolate. The tepal apex is acuminate. The tepal base is typically acute.
- *Apex recurvature.*—Slightly recurved.
- *Tepal cross section.*—Cupped.
- *Margins.*—Entire.
- *Tepal overlap.*—Almost none.
- *Persistence.*—Tepals drop off cleanly.

Reproductive organs:
- *Pollen.*—None observed.
- *Anthers.*—Size: 5 mm in length. Color: Red-Purple Group 59A. Quantity: On average, 120.
- *Filaments.*—Color: Yellow Group 2D. Length: 5 to 10 mm.
- *Pistils.*—Quantity: On average, 65.
- *Stigmas.*—Superior in location relative to the length of the filaments and the height of the anthers. Color: Yellow Group 3D.
- *Styles.*—Color: Yellow Group 3D. Length: 10 mm.

Seed head characteristics:
- *Size.*—40 mm in height. 40 mm in diameter.
- *Quantity.*—About 20 seeds produced per seed head.
- *Style appearance.*—Plumose, semi-erect.

PLANT

Plant form: Climbing.

Plant growth: Vigorous.

Size: Seasons growth attains 130 to 150 cm in height. Average spread is 50 cm.

Stems:
- *Color.*—Juvenile stems are Yellow-Green Group 144A. Mature stems are Greyed-Purple Group 183A.
- *Internodes.*—On average, 9 to 12 cm between nodes.
- *Length.*—Normally 50 cm from the base of the plant to the flowering portion of the stem.
- *Diameter.*—About 2 mm.
- *Texture.*—Mature stems are smooth.

Plant foliage:
- *Leaf characteristics.*—Deciduous.
- *Arrangement.*—Ternate.
- *Leaf size.*—Compound leaves are about 90 to 150 mm (l)×80 to 160 mm (w). Leaflets are about 40 to 65 mm (l)×15 to 30 mm (w).
- *Abundance.*—On average 1 or 2 leaves per 10 cm of stem.
- *Leaf color.*—Juvenile upper Yellow-Green Group 144A. Juvenile lower Yellow-Green Group 144B. Mature upper Yellow-Green Group 146A. Mature lower Yellow-Green Group 147B.
- *Stipules.*—Absent.
- *Petioles.*—Size: Normally 40 to 60 mm in length by 1 mm diameter. Texture: Smooth. Color: Yellow-Green Group 146C.
- *Petioloule.*—Size: About 10 to 35 mm in length by 1 to 2 mm diameter. Texture: Smooth. Color: Yellow-Green Group 146C.
- *Leaflet shape.*—Cordate. The base is cordate or oblique. The apex is acute.
- *Margin.*—Entire.
- *Surface.*—The upper side is smooth, the lower side is smooth.
- *Thickness.*—Moderate.
- *Glossiness.*—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo092', substantially as described and illustrated, due to its abundant red purple flowers with good keepability, attractive long lasting foliage and compact growth, suitability for production from softwood cuttings in pots, durable flowers and foliage which make the variety suitable for distribution in the floral industry.

* * * * *

'Evipo092'

'Evipo092'